US006653618B2

United States Patent
Zenzie

(10) Patent No.: US 6,653,618 B2
(45) Date of Patent: Nov. 25, 2003

(54) CONTACT DETECTING METHOD AND APPARATUS FOR AN OPTICAL RADIATION HANDPIECE

(75) Inventor: Henry M. Zenzie, Dover, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 253 days.

(21) Appl. No.: 09/847,043

(22) Filed: Apr. 30, 2001

(65) Prior Publication Data

US 2002/0005475 A1 Jan. 17, 2002

Related U.S. Application Data

(60) Provisional application No. 60/200,431, filed on Apr. 28, 2000.

(51) Int. Cl.[7] .......................... G06M 7/00; A61B 18/18
(52) U.S. Cl. ........................... 250/221; 606/9; 606/12
(58) Field of Search ........................... 250/216, 221, 250/222.1, 229; 606/2, 9, 12

(56) References Cited

U.S. PATENT DOCUMENTS

| | | |
|---|---|---|
| 3,327,712 A | 6/1967 | Kaufman et al. |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,049,964 A | * 9/1977 | Wuchinich et al. ......... 250/221 |
| 4,233,493 A | 11/1980 | Nath |
| 4,273,109 A | 6/1981 | Enderby |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |

(List continued on next page.)

FOREIGN PATENT DOCUMENTS

| | | |
|---|---|---|
| AT | 400305 B | 4/1995 |
| DE | 3837248 A1 | 5/1990 |
| EP | 0142671 A1 | 5/1985 |

(List continued on next page.)

OTHER PUBLICATIONS

G.B. Altshuler et al., "Acoustic response of hard dental tissues to pulsed laser action," SPIE, vol. 2080, Dental Application of lasers, pp. 97–103, 1993.

G.B. Altshuler et al., "Extended theory of selective photothermolysis," Lasers in Surgery and Medicine, vol. 29, pp. 416–432, 2001.

R.L. Amy & R. Storb, "Selective mitochondrial damage by a ruby laser microbeam: An electron microscopic study," Science, vol. 15, pp. 756–758, Nov. 1965.

(List continued on next page.)

Primary Examiner—Huy Mai
(74) Attorney, Agent, or Firm—Thomas J. Engellenner; Deborah A. Miller; Nutter McClennen & Fish LLP

(57) ABSTRACT

A method and apparatus are provided in a system for utilizing optical radiation which is applied to a handpiece in contact with a patient's skin to perform a dermatological treatment on the patient to protect the patient by assuring that radiation is applied only when there is good contact between the handpiece and the patient's skin. Good contact is detected by detecting light at a skin contacting surface of the handpiece and enabling the application of radiation only if the detected light is within a selected range. The apparatus assures that the source is not normally enabled and is enabled only when it is safe to apply radiation, and in particular when there is good contact between the handpiece and the patient's skin.

17 Claims, 1 Drawing Sheet

U.S. PATENT DOCUMENTS

| | | |
|---|---|---|
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,747,660 A | 5/1988 | Nishioka et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,011,285 A * | 4/1991 | Jorgensen et al. .......... 356/335 |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,397,890 A * | 3/1995 | Schueler et al. ............ 250/221 |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,628,744 A * | 5/1997 | Coleman et al. ............ 606/12 |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,849,029 A | 12/1998 | Eckhouse et al. |
| 5,853,407 A | 12/1998 | Miller |
| 5,885,211 A | 3/1999 | Eppstein et al. |
| 5,885,273 A | 3/1999 | Eckhouse et al. |
| 5,885,274 A | 3/1999 | Fullmer et al. |
| 5,944,748 A | 8/1999 | Mager et al. |
| 5,948,011 A | 9/1999 | Knowlton |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A * | 1/2000 | Altshuler et al. ............... 606/9 |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson |
| 6,149,644 A | 11/2000 | Xie |
| 6,174,325 B1 | 1/2001 | Eckhouse |
| 6,197,020 B1 | 3/2001 | O'Donnell |
| 6,235,016 B1 | 5/2001 | Stewart |
| 6,236,037 B1 * | 5/2001 | Asada et al. ................. 250/221 |
| 6,273,884 B1 * | 8/2001 | Altshuler et al. ............... 606/9 |
| 6,273,885 B1 | 8/2001 | Koop et al. |
| 6,280,438 B1 | 8/2001 | Eckhouse et al. |
| 6,306,130 B1 | 10/2001 | Anderson et al. |
| 6,354,370 B1 | 3/2002 | Miller et al. |
| 6,508,813 B1 | 1/2003 | Altshuler et al. |
| 6,511,475 B1 | 1/2003 | Altshuler et al. |
| 6,517,532 B1 | 2/2003 | Altshuler et al. |
| 2002/0005475 A1 * | 1/2002 | Zenzie ....................... 250/221 |
| 2002/0091377 A1 | 7/2002 | Anderson et al. |
| 2002/0128635 A1 | 9/2002 | Altshuler et al. |
| 2002/0161357 A1 | 10/2002 | Anderson et al. |
| 2002/0173780 A1 | 11/2002 | Altshuler et al. |
| 2003/0023283 A1 | 1/2003 | McDaniel |
| 2003/0032950 A1 | 2/2003 | Altshuler et al. |
| 2003/0055414 A1 | 3/2003 | Altshuler et al. |
| 2003/0065314 A1 | 4/2003 | Altshuler et al. |

FOREIGN PATENT DOCUMENTS

| | | |
|---|---|---|
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |

| | | | |
|---|---|---|---|
| EP | 1038505 A2 | 9/2000 | |
| EP | 1219258 A1 | 3/2002 | |
| FR | 2591902 | 6/1987 | |
| GB | 2044908 A | 10/1980 | |
| GB | 2123287 A | 2/1984 | |
| GB | 2360946 A | 10/2001 | |
| RU | 2082337 C1 | 6/1997 | |
| RU | 2089126 C1 | 10/1997 | |
| RU | 2089127 C1 | 10/1997 | |
| RU | 2096051 C1 | 11/1997 | |
| RU | 2122848 C1 | 10/1998 | |
| WO | WO 86/02783 A1 | 5/1986 | |
| WO | WO 90/00420 A1 | 1/1990 | |
| WO | WO 91/13652 A1 | 9/1991 | |
| WO | WO 92/16338 A1 | 1/1992 | |
| WO | WO 92/19165 A1 | 11/1992 | |
| WO | WO 93/05920 A1 | 4/1993 | |
| WO | WO 95/15725 A1 | 6/1995 | |
| WO | WO 95/32441 A1 | 11/1995 | |
| WO | WO 96/23447 A1 | 8/1996 | |
| WO | WO 96/25979 A1 | 8/1996 | |
| WO | WO 97/13458 A1 | 4/1997 | |
| WO | WO 98/04317 A1 | 2/1998 | |
| WO | WO 98/24507 A2 | 6/1998 | |
| WO | WO 98/51235 A1 | 11/1998 | |
| WO | WO 98/52481 A1 | 11/1998 | |
| WO | WO 99/27997 A1 | 6/1999 | |
| WO | WO 99/29243 A1 | 6/1999 | |
| WO | WO 99/38569 A2 | 8/1999 | |
| WO | WO 99/46005 A1 | 9/1999 | |
| WO | WO 99/49937 A1 | 10/1999 | |
| WO | WO 00/03257 A1 | 1/2000 | |
| WO | WO 00/44294 A1 | 8/2000 | |
| WO | WO 00/71045 A1 | 11/2000 | |
| WO | WO 00/74781 A1 | 12/2000 | |
| WO | WO 00/78242 A1 | 12/2000 | |
| WO | WO 01/03257 A1 | 1/2001 | |
| WO | WO 01/34048 A1 | 5/2001 | |
| WO | WO 01/42671 A1 | 6/2001 | |
| WO | WO 01/54606 A1 | 8/2001 | |
| WO | WO 01/78830 A2 | 10/2001 | |
| WO | WO 02/53050 A1 | 7/2002 | |
| WO | WO 02/069825 A2 | 9/2002 | |
| WO | WO 02/094116 A1 | 11/2002 | |

OTHER PUBLICATIONS

R.R. Anderson et al., "The optics of human skin," Journal of Investigative Dermatology, vol. 77, No. 1, pp. 13–19, 1981.

R.R. Anderson & J.A. Parrish, "Selective photothermolysis: Precise microsurgery by selective absorption of pulsed radiation," Science, vol. 220, pp. 524–527, Apr. 1983.

A.V. Belikov et al., "Identification of enamel and dentine under tooth laser treatment," SPIE vol. 2623, Progress in Biomedical Optics Europt Series, Proceedings of Medical Applications of Lasers III, pp. 109–116, Sep. 1995.

J.S. Dover et al. "Pigmented guinea pig skin irradiated with Q–switched ruby pulses," Arch Dermatol, vol. 125, pp. 43–49, Jan. 1989.

L.H. Einkelstein & L.M. Blatstein, "Epilation of hair–bearing urethral grafts using the neodymium:yag surgical laser," Journal of Urology, vol. 146, pp. 840–842, Sep. 1991.

L. Goldman, Biomedical Aspects of the Laser, Springer–Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S–92–S–93, Jan.–Feb. 1965.

L. Goldman, "Effects of new laser systems on the skin," Arch Dermatol., vol. 108, pp. 385–390, Sep. 1973.

L. Goldman, "Laser surgery for skin cancer," New York State Journal of Medicine, pp. 1897–1900, Oct. 1977.

L. Goldman, "Surgery by laser for malignant melanoma," J. Dermatol. Surg. Oncol., vol, 5, No. 2, pp. 141–144, Feb. 1979.

L. Goldman, "The skin," Arch Environ Health, vol. 18, pp. 434–436, Mar. 1969.

L. Goldman & D.F. Richfield, "The effect of repeated exposures to laser beams," Acta derm.–vernereol., vol. 44, pp. 264–268, 1964.

L. Goldman & R.J. Rockwell, "Laser action at the cellular level," JAMA, vol. 198, No. 6, pp. 641–644, Nov. 1966.

L. Goldman & R.G. Wilson, "Treatment of basal cell epithelioma by laser radiation," JAMA, vol. 189, No. 10, pp. 773–775.

L. Goldman et al., "The biomedical aspects of lasers," JAMA, vol. 188, No. 3, pp. 302–306, Apr. 1964.

L. Goldman et al., "Effect of the laser beam on the skin, Preliminary report" Journal of Investigative Dermatology, vol. 40, pp. 121–122, 1963.

L. Goldman et al., "Effect of the laser beam on the skin, III. Exposure of cytological preparations," Journal of Investigative Dermatology, vol. 42, pp. 247–251, 1964.

L. Goldman et al., "Impact of the laser on nevi and melanomas," Archives of Dermatology, vol. 90, pp. 71–75, Jul. 1964.

L. Goldman et al., "Laser treatment of tattoos, A preliminary survey of three year's clinical experience," JAMA, vol. 201, No. 11, pp. 841–844, Sep. 1967.

L. Goldman et al., "Long–term laser exposure of a senile freckle," ArchEnviron Health, vol. 22, pp. 401–403, Mar. 1971.

L. Goldman et al., "Pathology, Pathology of the effect of the laser beam on the skin," Nature, vol. 197, No. 4870, pp. 912–914, Mar. 1963.

L. Goldman et al., "Preliminary investigation of fat embolization from pulsed ruby laser impacts of bone," Nature, vol. 221, pp. 361–363, Jan. 1969.

L. Goldman et al., "Radiation from a Q–switched ruby laser, Effect of repeated impacts of power output of 10 megawatts on megawatts on a tattoo of man," Journal of Investigative Dermatology, vol. 44, pp. 69–71, 1965.

L. Goldman et al., "Replica microscopy and scanning electron microscopy of laser impacts on the skin," Journal of investigative Dermatology, vol. 52, No. 1, pp. 18–24, 1969.

M.C. Grossman et al., "Damage to hair follicles by normal–mode ruby laser pulses," Journal of he American Academy of Dermatology, vol. 35, No. 6, pp. 889–894, Dec. 1996.

E. Klein et al., "Biological effects of laser radiation 1., " Northeast Electroncis Research and Engineering Meeting, NEREM Record, IEEE catalogue No. F–60, pp. 108–109, 1965.

J.G. Kuhns et al. "Laser injury in skin," Laboratory Investigation, vol. 17, No. 1, pp. 1–13, Jul. 1967.

J.G. Kuhns et al., "Biological effects of laser radiation II Effects of laser irradiation on the skin," Nerem Record, pp. 152–153, 1965.

R.J. Margolis et al., "Visible action spectrum for melanin–specific selective photothermolysis," Lasers in Surgery and Medicine, vol. 9, pp. 389–397, 1989.

J.A. Parrish, "Selective thermal effects with pulsed irradiation from lasers: From organ to organelle," Journal of Investigative Dermatology, vol. 80, No. 6 Supplement, pp. 75s–80s, 1983.

L. Polla et al., "Melanosomes are a primary target of Q–switched ruby laser irradiation in guinea pig skin," Journal of Investigative Dermatology, vol. 89, No. 3, pp. 281–286, Sep. 1987.

T. Shimbashi & T. Kojima, "Ruby laser treatment of pigmented skin lesions," Aesth. Plast. Surg., vol. 19, pp. 225–229, 1995.

Stratton, K., et al., "Biological Effects of Laser Radiation II: ESR Studies of Melanin Containing Tissues after Laser Irradiation," Northeast Electronics Research and Engineering Meeting—Nerem Record, IEEE Catalogue No. F–60, pp. 150–151, Nov. 1965.

C.R. Taylor et al., "Treatment of tattoos by Q–switched ruby laser," Arch. Dermatol. vol. 126, pp. 893–899, Jul. 1990.

V.V. Tuchin, "Laser light scattering in biomedical diagnostics and therapy," Journal of Laser Applications, vol. 5, No. 2–3, pp. 43–60, 1993.

S. Watanabe et al, "Comparative studies of femtosecond to microsecond laser pulses on selective pigmented cell injury in skin," Photochemistry and Photobiology, vol. 53, No. 6, pp. 757–762, 1991.

A.J. Welch et al., "Evaluation of cooling techniques for the protection of the pidermis during HD–yag laser irradiation of the skin," Neodymium–Yag Laser in Medicine and Surgery, Elsevier Science Publishing Co., publisher, pp. 195–204, 1983.

R.B. Yules et al., "The effect of Q–switched ruby laser radiation on dermal tattoo pigment in man," Arch Surg, vol. 95, pp. 179–180, Aug. 1967.

G.G. Riggle et al., "Laser effects on normal and tumor tissue," Laser Applications in Medicine and Biology, vol. I, M.L. Wolbarsht, editor, Plenum Press, publishers, Chapter 3, pp. 35–65, 1971.

Abstracts Nos. 17–19, Lasers in Surgery and Medicine, ASLMS, Supplement 13, 2001.

Abstracts Nos. 219–223, ASLMS.

Abstracts, various.

Invention description to certificate of authorship, No. 532304, "The way of investigation of radiation time structure of optical quanturn generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no–linearity of an index of refraction of optical medium".

Invention description to certificate of authorship, No. SU 1326962 A1, "The way of determination of non–linearity of an index of refraction of optical medium".

Zeitler, E. and Wolbarsht, M. L., "Laser Characteristics that Might be Useful in Biology," *Laser Applications in Medicine and Biology*, 1:1–16, 1971.

* cited by examiner

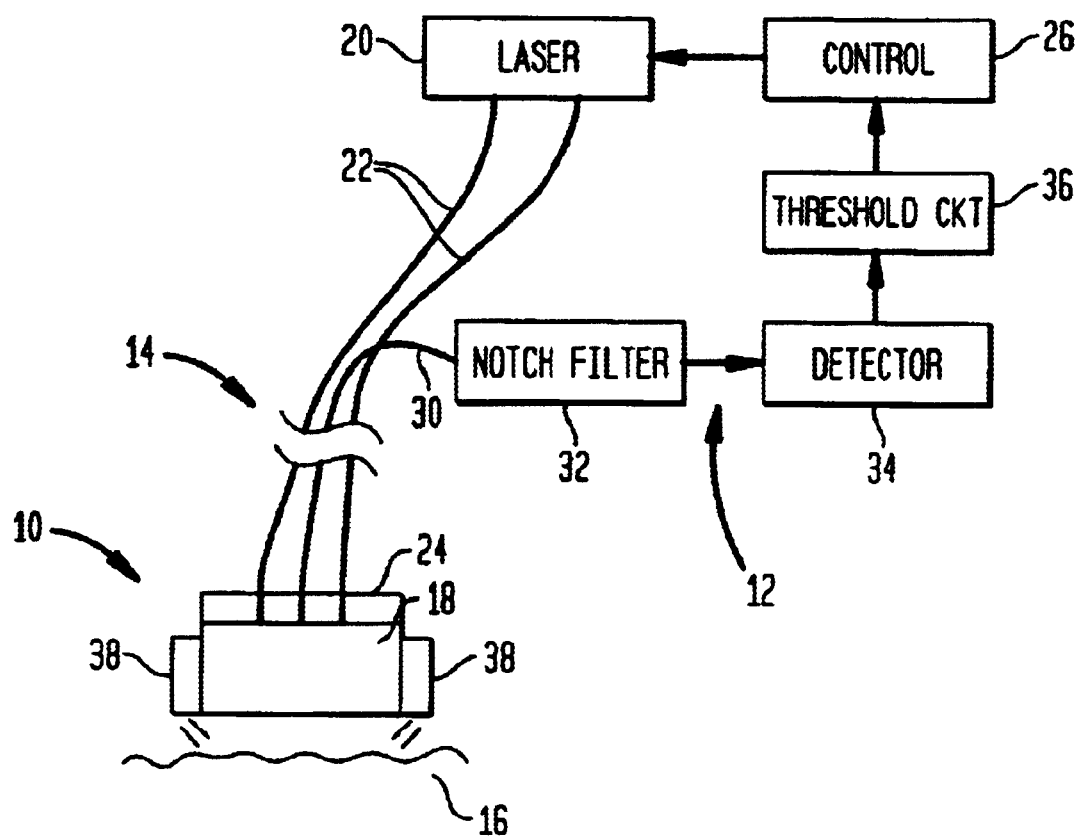

CONTACT DETECTING METHOD AND APPARATUS FOR AN OPTICAL RADIATION HANDPIECE

PRIOR APPLICATION

This application claims priority from provisional application Ser. No. 60/200,431 filed Apr. 28, 2000.

FIELD OF THE INVENTION

This invention relates to optical dermatology and more particularly to methods and apparatus for detecting skin contact with an optical radiation handpiece.

BACKGROUND OF THE INVENTION

Where lasers or other optical radiation sources, such as flashlamps, are utilized to perform a dermatological procedure, it is important, for many such procedures, that good physical, optical and/or thermal contact be made and maintained between a handpiece delivering the optical radiation and the patient's skin. Such contact accomplishes at least three things. First, since a controlled amount of radiant energy is delivered for a selected time period for most dermatological procedures in order to achieve the desired result, if there is not good optical contact with the skin, the applied radiation will not be efficiently optically coupled to the skin and the patient will therefore receive less radiation than intended. This may negatively impact the efficacy of the treatment. Second, since radiation applied to the dermis or below must pass through the epidermis, there is a danger of epidermal damage for many optical dermatology treatments. The damage threshold for epidermal damage may be raised by cooling the epidermis, preferably both before and during treatment. This is frequently done by cooling a handpiece in contact with the patient's skin through which the optical radiation is applied, good thermal contact between the handpiece and the patient's skin being required for such contact cooling to be effective. Therefore, the protocol for such treatments generally requires that the laser or other optical source not be fired until good contact between the handpiece and the skin has been established for a selected minimum time interval. Third, particularly where a laser is used, the radiation source may cause damage to eyes or other parts of the body if unintentionally fired when not in contact with the patients skin.

Therefore, for at least one of the above reasons, and frequently for two or more of these reasons, good contact with the patient's skin is generally a required condition for permitting firing of the radiation source in an optical dermatology procedure. While a number of procedures have been utilized in the past for detecting contact with the patient's skin, many such procedures have been complicated, expensive, and have not always been effective. Further, some of these procedures have not only permitted firing when there is contact, but have also permitted firing when there is some fault in the system. However, since firing only when there is good contact is a safety issue, this is generally not acceptable, it being required that the laser or other light source only fire when there is good contact and under no other condition, the default condition of the system being that the source is not firing. A need therefore exists for improved methods and apparatus for contact detection between a handpiece used in an optical dermatology system and a patient's skin which overcome the various deficiencies indicated above.

SUMMARY OF THE INVENTION

In accordance with the above, this invention, in accordance with one aspect thereof, provides apparatus for use in a system for utilizing optical radiation applied through a handpiece in contact with a patient's skin to perform a dermatological treatment on the patient, the apparatus assuring good contact between the handpiece and the patient's skin when radiation is applied. The apparatus includes a detector for picking up at least selected light at a skin-contacting surface of the handpiece and a control which enables application of the radiation only when light detected by the detector is within a selected range. The detector may be in the handpiece or may be in a console connected to the handpiece through an umbilical, an optical fiber being provided in the latter instance in the umbilical for transmitting light from the interior of the handpiece to the detector. A notch filter may be positioned to prevent radiation at the selected wavelength of an optical radiation source from reaching the detector, the selected light being at a wavelength other than the selected wavelength. The selected light may be ambient light or a source of the selected light may be provided which is positioned so that light from the source enters the handpiece when the handpiece is not in contact with the patient's skin but is substantially blocked from entering the handpiece when the handpiece is in good contact with the patient's skin. The light source may be at a wavelength or at a wavelength band other than that of the optical radiation and a filter may be provided which blocks all radiation from being applied to the detector other than radiation at the wavelength or wavelength band of the source. The handpiece is preferably designed to substantially prevent all of the selected light from entering the handpiece when the handpiece is in good contact with the patient's skin. The control may enable application of radiation only when the light detected by the detector is below a selected threshold, but preferably enables application of radiation when the light detected by the detector is both below a selected first threshold and above a second much lower threshold.

In accordance with another aspect of the invention, a method is provided for assuring good contact between a handpiece and a patient's skin before radiation is applied, the method being utilized in an optical radiation system of the type indicated above and including enabling application of the radiation only when selected light detected in the handpiece is within a selected range. More specifically, the method includes thresholding said detected light, and utilizing the results of the thresholding to control the application of radiation. The applying of the selected light to the handpiece is preferably done in a manner such that light enters the handpiece when the handpiece is not in contact with the patient's skin but is substantially blocked from entering the handpiece when the handpiece is in good contact with the patient's skin. More particularly, the selected light applied to the handpiece is preferably from a source of a wavelength or wavelength band other than that of the optical radiation and all radiation other than the radiation at the wavelength or wavelength band of the selected light is filtered, the filtered radiation being applied to a detector which generates an output when the radiation is within the selected range. The control preferably enables application of radiation only when the selected light detected in said handpiece is both below a selected first threshold and above a second much lower threshold.

In accordance with still another aspect of the invention, apparatus is provided for protecting the patient in a system of the type indicated above which apparatus includes a mechanism for assuring that radiation from the source is not normally applied to the handpiece, a mechanism for detecting when it is safe to apply radiation from the source to the handpiece and a mechanism which is operative in response to the detecting mechanism for enabling application of radiation from the source to the handpiece.

The foregoing and other objects, features and advantages of the invention will be apparent from the following more particular description of a preferred embodiment of the invention as illustrated in the accompanying drawing.

IN THE DRAWINGS

The FIGURE is a schematic representation of an illustrative embodiment of the invention.

DETAILED DESCRIPTION

Referring to the FIGURE, a handpiece 10 is provided which is connected to a console 12 through an umbilical 14. The handpiece is used to deliver optical radiation to the skin 16 of a patient. The handpiece includes an optical system 18 which, depending on the particular handpiece, may include one or more lenses, waveguides and the like for directing, and sometimes focusing, optical radiation received from a laser or other optical radiation source 20 through optical fibers 22 of umbilical 14 to the patient's skin 16. Optical fibers 22 terminate in a plate or other suitable termination 24 for the fibers, such terminations being known in the art. The firing of laser 20 is controlled by a suitable control device 26, for example a microprocessor. Optical system 18 frequently includes a plate or waveguide in contact with the patient's skin which is cooled by flowing water or gas, by a thermoelectric device, or by other suitable means to cool the skin in contact therewith. Such plate/waveguide is generally of a material having good optical and thermal transmission properties and preferably a good optical match with skin, sapphire being one such material.

In accordance with the teachings of this invention, an additional optical fiber 30 terminates in termination plate 24 and extends through umbilical 14 to a notch filter 32 in console 12. Fiber 30 is for the illustrative embodiment 0.37 NA or larger, preferably about 600 microns, to maximize the amount of light collected from the optical system 18 of the handpiece. Notch filter 32 is provided to filter out radiation at the wavelength of laser or other optical source 20. Radiation passing through notch filter 32 is applied to an optical detector 34, for example a silicon detector. The output of optical detector 34 is applied through a threshold detector or other suitable threshold circuit 36 as an input to control 26.

For an illustrative embodiment, when handpiece 18 is not in contact with the patient's skin 16, ambient light entering optical system 18 causes detector 34 to generate an output of for example 60 millivolts or more. However, with handpiece 18 being designed so that ambient light cannot enter optical system 18 when the handpiece is in good physical, optical and thermal contact with skin 16, detector 34 may generate an output of only 2 millivolts. For such an embodiment, threshold circuit 32 might be set with a cutoff of 5 millivolts, so that it would generate an output to control 26, enabling the firing of laser 20, only when its input from detector 34 was 5 millivolts or less. Thus, the laser would not fire unless there was good contact between the handpiece and the patient's skin. The values indicated above are of course only for an illustrative embodiment and the actual threshold value for a particular handpiece would most easily be empirically determined.

However, the system described to this point could generate outputs from the threshold detector under various fault conditions of the system, a condition which, as indicated above, is undesirable. For example, ambient light conditions at the handpiece can vary widely, adversely affecting the sensitivity of the contact sensor. Thus, for example if the person administers the procedure while standing over the handpiece, a not uncommon situation, ambient light could be blocked, preventing the detection of a slight loss of contact between handpiece and skin Therefore, for preferred embodiments, a light source is provided close to the handpiece which creates a fixed ambient light level. The light source can be a single lamp, a fiber-coupled lamp or a diode laser whose wavelength is not significantly attenuated by notch filter 32. For the illustrative embodiment shown in the FIGURE, light source 38 is shown as incorporated into handpiece 10, two such sources being shown for purposes of illustration. Depending on the nature of the light source, their number and location might vary. However, it is desirable that the number and location be sufficient to provide substantially uniform illumination so that a failure to make good contact at any point along the handpiece will result in light in excess of the threshold reaching detector 34.

If light sources 38 are low energy laser diodes of a wavelength different from that of laser 20, or a filtered light source which passes a limited wavelength of light different from that of laser 20, then notch filter 32 could be a bandpass filter which passes only the wavelength or wavelength band of source 38, making the system impervious to variations in ambient light from whatever cause. Further, threshold circuit 36 preferably has both an upper limit and a lower limit, generating an output only when the detector output is between these limits. For the example previously discussed, the upper limit could remain 5 millivolts and a lower limit of 1 millivolt or 0.5 millivolts could also be provided so that if light source 38 failed, there was a break in fiber 30 or some other failure occurred in the system, there would be no output from threshold circuit 36, and the laser would not fire.

While notch filter 32, detector 34 and threshold circuit 36 have been shown as being in console 12 for the illustrative embodiment, this is not a limitation on the invention and, for example, notch filter 32 and detector 34 could be located in handpiece 18. A potential problem with this embodiment is that an electrical line passing through umbilical 14 might be subject to noise, making the detection less precise. Such noise could be dealt with in various ways known in the art, including having the electrical lead as a twisted pair. This problem could also be reduced by having threshold circuit 36 also located in the handpiece.

Other variations in the embodiment shown are also possible. For example, threshold circuit 36 may be part of controls 26, the processor of controls 26 being programmed to perform the threshold function. Depending on the particular handpiece used, two or more fibers 30 might be employed to collect ambient light and the termination for these fibers and the location of such terminations may be substantially varied.

Thus, while the invention has been particularly shown and described above with reference to an illustrative embodiment, the foregoing and other changes in form and detail may be made therein by one skilled in the art without departing from the spirit and scope of the invention which is to be defined only by the following claims.

What is claimed is:

1. In a system for utilizing optical radiation applied through a handpiece in contact with a patient's skin to perform a dermatological treatment on the patient, apparatus for assuring good contact between the handpiece and the patient's skin when said radiation is applied, said apparatus including:

a detector for picking up at least selected light at a skin-contacting surface of said handpiece; and a control which enables application of said radiation only when light detected by said detector is within a selected range.

2. Apparatus as claimed in claim 1 wherein said detector is in said handpiece.

3. Apparatus as claimed in claim 1 wherein said detector is in a console connected to said handpiece through an umbilical, said umbilical including an optical fiber transmitting light from the interior of the handpiece to said detector.

4. Apparatus as claimed in claim 1 wherein said optical radiation is at a selected wavelength, and wherein said system includes a notch filter positioned to prevent radiation at said selected wavelength from reaching said detector.

5. Apparatus as claimed in claim 4 wherein said selected light includes light at a wavelength other than said selected wavelength.

6. Apparatus as claimed in claim 1 wherein said selected light includes ambient light.

7. Apparatus as claimed in claim 1 including a source of said selected light positioned so that light from said source enters said handpiece when the handpiece is not in contact with a patient's skin, but is substantially blocked from entering the handpiece when the handpiece is in good contact with the patient's skin.

8. Apparatus as claimed in claim 7 wherein the selected light from said source is one of a wavelength and a wavelength band other than that of said optical radiation, and wherein said system includes a filter which blocks all radiation from being applied to said detector other than radiation at said wavelength/wavelength band.

9. Apparatus as claimed in claim 1 wherein said handpiece is designed to substantially prevent said selected light from entering the handpiece when said handpiece is in good contact with the patient's skin.

10. Apparatus as claimed in claim 1 wherein said control enables application of radiation only when light detected by said detector is below a selected threshold.

11. Apparatus as claimed in claim 10 wherein said control enables application of radiation only when light detected by said detector is both below said selected threshold and above a second much lower threshold.

12. In a system for utilizing optical radiation applied through a handpiece in contact with a patient's skin to perform a dermatological treatment on the patient, a method for assuring good contact between the handpiece and the patient's skin before said radiation is applied, said method including enabling application of said radiation only when selected light intensity detected in said handpiece is within a selected range.

13. A method as claimed in claim 12 including detecting said selected light intensity in the handpiece;

thresholding said detected light intensity; and utilizing the results of the thresholding to control said application of radiation.

14. A method as claimed in claim 12 including applying said selected light to said handpiece in a manner such that light enters said handpiece when the handpiece is not in contact with a patient's skin, but is substantially blocked from entering the handpiece when the handpiece is in good contact with the patient's skin.

15. A method as claimed in claim 12 wherein the selected light applied to said handpiece is from a source of one of a wavelength and a wavelength band other then that of said optical radiation, and including the steps of filtering all radiation other then radiation at said wavelength/wavelength band, and applying radiation from said filtering step to a detector which generates an output when the radiation is within said selected range.

16. A method as claimed in claim 12 wherein application of radiation is enabled only when said selected light detected in said handpiece is both below a selected first threshold and above a second lower threshold.

17. In a system for utilizing optical radiation from a source applied through a handpiece in contact with a patient's skin to perform a dermatological treatment on the patient, apparatus for protecting the patient including:

a mechanism utilizing at least selected light in said handpiece for assuring that radiation from said source is not normally applied through said handpiece;

a mechanism for detecting good contact between the handpiece and the patient's skin; and a mechanism operative in response to said detecting mechanism for enabling application of radiation from said source through said handpiece.

* * * * *